United States Patent
Miller et al.

(10) Patent No.: US 9,855,165 B2
(45) Date of Patent: Jan. 2, 2018

(54) INTERRUPTING THE LIFE CYCLE OF SPERM

(71) Applicant: SoundHealth, LLC, Boca Raton, FL (US)

(72) Inventors: Michael R. Miller, Boca Raton, FL (US); Robert Sewak, Boca Raton, FL (US)

(73) Assignee: SOUND TECHNOLOGY TRANSFER, LLC, Boca Raton, FL (US)

( * ) Notice: Subject to any disclaimer, the term of this patent is extended or adjusted under 35 U.S.C. 154(b) by 0 days.

(21) Appl. No.: 14/703,001

(22) Filed: May 4, 2015

(65) Prior Publication Data

US 2016/0324682 A1  Nov. 10, 2016

(51) Int. Cl.
*A61F 6/04* (2006.01)
*A61F 6/02* (2006.01)

(52) U.S. Cl.
CPC ..................................... *A61F 6/02* (2013.01)

(58) Field of Classification Search
CPC ...... A61F 6/00; A61F 6/02; A61F 6/04; A61F 6/065; A61F 5/41; A61F 2006/042
See application file for complete search history.

(56) References Cited

U.S. PATENT DOCUMENTS

| | | | |
|---|---|---|---|
| 4,078,556 A | 3/1978 | Fahim | |
| 8,090,129 B2* | 1/2012 | Yu | G11B 31/02 381/124 |
| 2009/0171138 A1 | 7/2009 | Eli | |
| 2010/0001568 A1* | 1/2010 | Trybus | B60N 2/1835 297/312 |
| 2010/0089406 A1 | 4/2010 | Kachiguina | |

(Continued)

FOREIGN PATENT DOCUMENTS

WO  2007019560 A2  2/2007

OTHER PUBLICATIONS

Vandevoort, et. al. The Efficacy of Ultrasound Treatment as a Reversible Male Contraceptive in the Rhesus Monkey. Article, Reproductive Biology arid Endocrinology, vol. 10, No. 81, Sep. 12, 2012 (online) (Claims 10-16; 19-20; 1-9; 17-18).

(Continued)

*Primary Examiner* — Ophelia A Hawthorne
(74) *Attorney, Agent, or Firm* — The Concept Law Group, P.A.; Scott D. Smiley (57) ABSTRACT

A method of interrupting the life cycle of sperm that includes subjecting a user to a first and a second treatment session in a male birth-control cycle. The first treatment session including a mature-sperm inhibition step of emitting, through at least one transducer, an amount energy for a predetermined period of time that is directed to the entire male reproductive system including but not limited to at least one of an epididymal tubules and an ejaculation ducts of the user, via a constant coupling configuration of the transducer with the user, to render a plurality of sperm transported therein to be immotile. The second treatment session includes subjecting the user to the mature-sperm inhibition step before a sperm-maturation time whereby sperm carried by the user are in a mature state.

19 Claims, 6 Drawing Sheets

(56) References Cited

U.S. PATENT DOCUMENTS

| | | | |
|---|---|---|---|
| 2010/0320819 A1* | 12/2010 | Cohen | A61H 23/0236 297/217.4 |
| 2011/0061661 A1* | 3/2011 | Hayes | A47G 9/1045 128/845 |
| 2013/0079584 A1* | 3/2013 | Armbruster | A61M 21/02 600/28 |

OTHER PUBLICATIONS

Sharma, R. and Agarwal, A., Spermatogenesis: An Overview. Sperm Chromatin (online) Journal, Chapter 2, p. 20, ISBN:978-1-4419-6857-9 (Claims 1-20).

* cited by examiner

FIG. 6

INTERRUPTING THE LIFE CYCLE OF SPERM

FIELD OF THE INVENTION

The present invention relates generally to birth control techniques and, more particularly relates to a method and device for interrupting the life cycle of sperm.

BACKGROUND OF THE INVENTION

It is well known that the reproduction of offspring includes packing, storing, and passing on deoxyribonucleic acid (DNA). The transmission of DNA occurs through reproductive cells called gametes, which are the haploid germ cells of males and females. Gametes are produced during meiosis and contain half of the parental chromosomes. Each gender produces its own gamete with only half of its genetic material. Female gametes are commonly referred to as ova or egg cells and male gametes are commonly referred to sperm. During reproduction, the ova or egg cells combine with the sperm to produce offspring, each offspring having approximately half of the DNA of the female and half of the DNA of the male.

The male reproductive process begins within the brain. The first major step in the male reproductive process is the production of Gonadotropin-releasing hormone (GnRH), also known as Luteinizing-hormone-releasing hormone (LHRH), within the hypothalamus. GnRH is a trophic peptide hormone responsible for the release of follicle-stimulating hormone (FSH) and luteinizing hormone (LH) from the anterior pituitary. FSH is responsible for maintaining sperm production, while LH is responsible for stimulating the production of the male hormone testosterone.

The production of both sperm and testosterone occurs in the testicles, or testis (singular), contained in the scrotal sac, often referred to as the scrotum. The scrotal sac develops on the outside of the body because the normal body temperature of a human male is too high to permit proper sperm production to occur within the body. Sperm are manufactured in several hundred microscopic tubes, known as seminiferous tubules, which make-up the majority of the testicles. Leydig cells, located adjacent to the seminiferous tubules, produce the testosterone in the presence of LH.

The life cycle of the sperm begins partially embedded in Sertoli cells, located in the lower region of the seminiferous tubules. As the sperm begins to mature, the sperm is stored in the upper region of the seminiferous tubules. Young sperm cells are commonly known as spermatids. Following the development of the head and the tail, the sperm is released from the Sertoli cell into the Epididymis where the sperm matures. A mature sperm contains a tail, a mid-piece and a head.

The Epididymis is a single, narrow, tightly-coiled tube that is normally approximately 15 to 20 feet in length. The diameter of the epididymal tubules is only approximately 200 microns. The Epididymis loops back and forth on itself within a space that is only about 1.5 inches in length. The sperm's journey to maturity through the Epididymis takes approximately 3 weeks. The fluid in which the sperm is transported contains sugar in the form of fructose, which provides energy as the sperm matures. In the early stages of sperm motility, the sperm cannot swim in a forward and straight direction, rather, the sperm is moved through the male reproductive tract by muscle contraction. By the time the sperm reaches the end of the Epididymis, however, the sperm can swim straight and forward through the use of the tail. Sperm motility, i.e., the ability of the sperm to move, in a forward and straight direction in a rapid manner is a significant element of male fertility. The head of the sperm contains the male's genetic material, i.e., DNA. The vas deferens, or vasa deferentia (plural), is the part of the male anatomy that transports the sperm from the epididymis to the ejaculatory ducts in anticipation of ejaculation. The time it takes for sperm to reach the ejaculatory ducts is approximately 74 days, during which maturation takes place. Research indicates that in order for a sperm to naturally fertilize an egg or ova, the sperm has to be mature.

There are various known devices and methods to prevent or reduce the likelihood of pregnancy. Some devices and methods are directed toward the female reproductive organs or track. Many of these devices and methods, however, are invasive. Alternatively, many consumers or patients desire a birth control device or method directed to a male's reproductive organs or track. One such male birth control method includes a vasectomy.

A vasectomy is essentially a surgical procedure for male sterilization, often referred to as permanent birth control. The vas deferens plays an essential role in the vasectomy procedure. During a vasectomy, the vas deferens on each testicle is clamped, cut, or otherwise sealed so as to prevent sperm from entering into the seminal stream. Said another way, the sperm are prevented from mixing with the semen that is ejaculated from the penis. The testicles continue to produce sperm, however the sperm are reabsorbed by the body. Unfortunately, it normally takes several months after a vasectomy for all remaining sperm track to be ejaculated and/or reabsorbed by the body. As such, another method of birth control must be utilized until a semen sample shows a zero sperm count. The failure to use another method of birth control may result in pregnancy. Moreover, scrotal pain may occur following a vasectomy. A number of males experience chronic pain that may include sore testicles, including epididymitis, for a period lasting as long as a year following the vasectomy.

As with many surgical procedures, there are also a number of risks associated with a vasectomy. The risks include, but are not limited to, bleeding under the skin that causes swelling or bruising, infection at the site of the incision or inside the scrotum, and even leaking from the vas deferens into the surrounding tissue. The leakage may produce a small lump called sperm granuloma which requires medical attention. As an added problem, the vasectomy is costly and may not be covered by medical insurance. In the event a male seeks to have the vasectomy reversed, surgery is required to reconnect the vas deferens. This type of surgery is costly and often difficult to perform additionally recent studies have established a linkage to these types of procedures to negative effects on the prostate.

Another existing method of providing male sterilization is through the blocking of the vas deferens with a chemical or physical plug, as opposed to the cutting of the vas deferens which occurs during a vasectomy. This method, however, is often not completely effective for male sterilization.

There are also other known devices and methods of male birth control that include condoms and attaching a device at the distal end of the male's penis that captures the semen as it is ejaculated. There are common disadvantages, however, to these methods and devices. These disadvantages include attachment to the penis each time before intercourse and/or discomfort to one or more parties involved in intercourse.

Therefore, a need exists to overcome the problems with the prior art as discussed above.

SUMMARY OF THE INVENTION

The invention provides a method and device of interrupting the life cycle of sperm that overcomes the hereinabove-mentioned disadvantages of the heretofore-known devices and methods of this general type and that temporarily, and with minimal invasiveness, causes sperm contained within a male's reproductive track to die or otherwise to become immotile, thereby creating an advantageous state of infertility.

In accordance with the present invention, a method of interrupting a life cycle of sperm has been disclosed that includes subjecting a user to a (1) first treatment session in a male birth-control cycle that includes a mature-sperm inhibition step of emitting, through at least one transducer, an amount of energy for a predetermined period of time that is directed to at least one of an epididymal tubules and an ejaculation ducts of the user, via a constant coupling configuration of the transducer with the user, to render a plurality of sperm transported therein to be immotile and then (2) subjecting the user to a second treatment session within the male birth-control cycle before a sperm-maturation time whereby sperm carried by the user are in a mature state. The second treatment session also includes the mature-sperm inhibition step.

In accordance with another feature, an embodiment of the present invention includes the mature-sperm inhibition step having the sub-step of directing the amount of energy at a predetermined minimum intensity sufficient to propagate the amount of energy to the at least one of an epididymal tubules and an ejaculation ducts of the user to render the plurality of sperm transported therein to be immotile.

In accordance with a further feature of the present invention, the predetermined minimum intensity of the amount of energy is an equivalent of approximately five watts.

In accordance with yet another feature of the present invention, the sperm-maturation time is within seventy-four, sixty, or thirty days after subjecting the user to the first treatment session in the male birth-control cycle.

In accordance with an additional feature, an embodiment of the present invention includes the mature-sperm inhibition step having the sub-step of providing a cushion having a top surface sized to receive buttocks of the user, wherein the cushion is in a covering relationship with the transducer. The mature-sperm inhibition step may also then include positioning the buttocks of the user on the top surface of the cushion, wherein the cushion may encapsulate the transducer.

In accordance with a further feature of the present invention, the amount of energy is of an oscillating sound pressure wave in an acoustic frequency range.

In accordance with a further feature of the present invention includes the mature-sperm inhibition step having the sub-step of modulating a frequency of the oscillating sound pressure wave at a point in time $T_1$ within the predetermined period of time to generate a first-modulated sound pressure wave having a frequency greater than the frequency of the oscillating sound pressure wave. Another sub-step may include modulating the frequency of the first-modulated sound pressure wave at a point in time $T_2$ within the predetermined period of time to generate a second-modulated sound pressure wave having a frequency greater than the frequency of the first-modulated sound pressure wave. The point in time $T_2$ may also be later than the point in time $T_1$.

In accordance with an additional feature of the present invention, the amount of energy is of at least three oscillating sound pressure waves in a predetermined harmonic frequency sequence.

In accordance with yet another feature, an embodiment of the present invention includes the mature-sperm inhibition step having the sub-step of emitting, through the at least one transducer, a series of modulated amounts of energy for the predetermined period of time. The series of modulated amounts of energy may include a plurality of oscillating sound pressure waves in an acoustic frequency range. Moreover, the plurality of oscillating sound pressure waves may be vary in frequency.

In accordance with a further feature, an embodiment of the present invention includes providing a controller electrically coupled to the at least one transducer, wherein the controller is operably configured to provide timing and duration optimization to the at least one transducer.

In accordance with an additional feature, another embodiment of the present invention includes executing a program, by a processor communicatively coupled to the controller, the program having steps that include initiating a first phase that includes the emission of the amount of energy through the at least one transducer and a second phase that includes a cessation of the emission of the amount of energy through the at least one transducer at a conclusion of the predetermined period of time.

In accordance with yet another feature, an embodiment of the present invention includes (1) emitting, through the at least one transducer, a series of modulated amounts of energy for the predetermined period of time (with the series of modulated amounts of energy including a plurality of oscillating sound pressure waves, of varying frequencies, in an acoustic frequency range) and (2) executing a program, by a processor communicatively coupled to the controller, the program having steps that include initiating a first phase that includes the emission of the amount of energy through the at least one transducer, a modulation phase that includes emitting the series of modulated amounts of energy with the plurality of oscillating sound pressure waves, of varying frequencies, in the acoustic frequency range, and a second phase that includes a cessation of the emission of the amount of energy through the at least one transducer at a conclusion of the predetermined period of time.

In accordance with another feature, an embodiment of the present invention includes receiving, at the processor resident on a computing device of a user, an initiation signal directing the processor to initiate the first phase of the program.

Although the invention is illustrated and described herein as embodied in a method and device of interrupting the life cycle of sperm, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of a user with reference to a ground surface to which that user stands or is seated. The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient method, device, and system of interrupting the life cycle of sperm. While the principal embodiment of the invention is used for interrupting the life cycle of sperm, other variations of the present invention can be used to provide a method of female birth control, pain management, and stimulating the flow of blood and other fluids contained within the body of a user.

Figure 1:
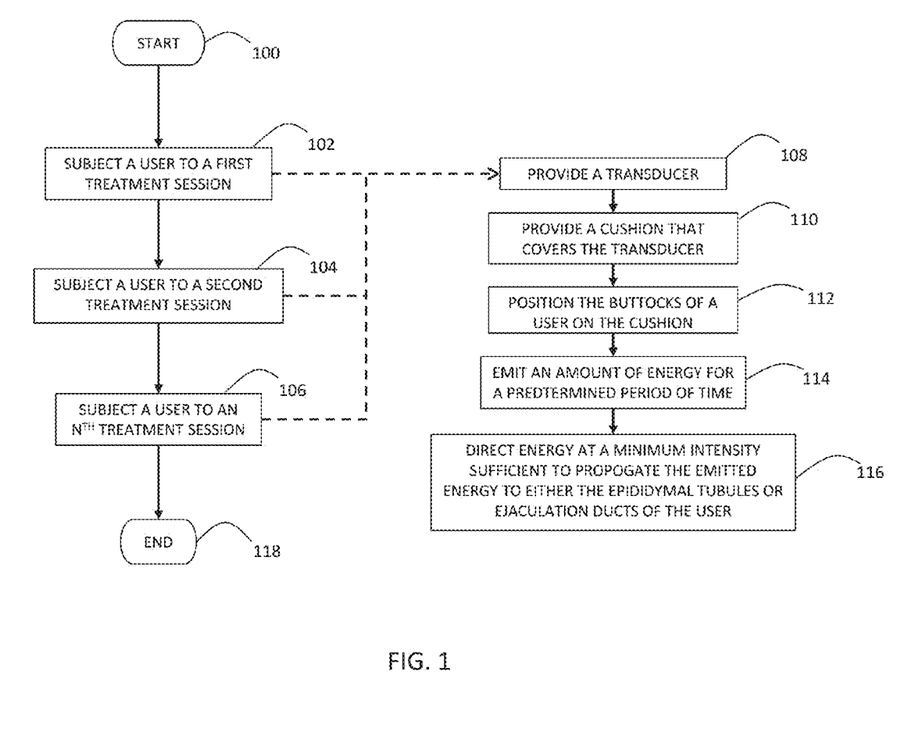
FIG. 1 is a process-flow diagram of a method of interrupting the life cycle of sperm in accordance with one embodiment of the present invention.
Figure 2:
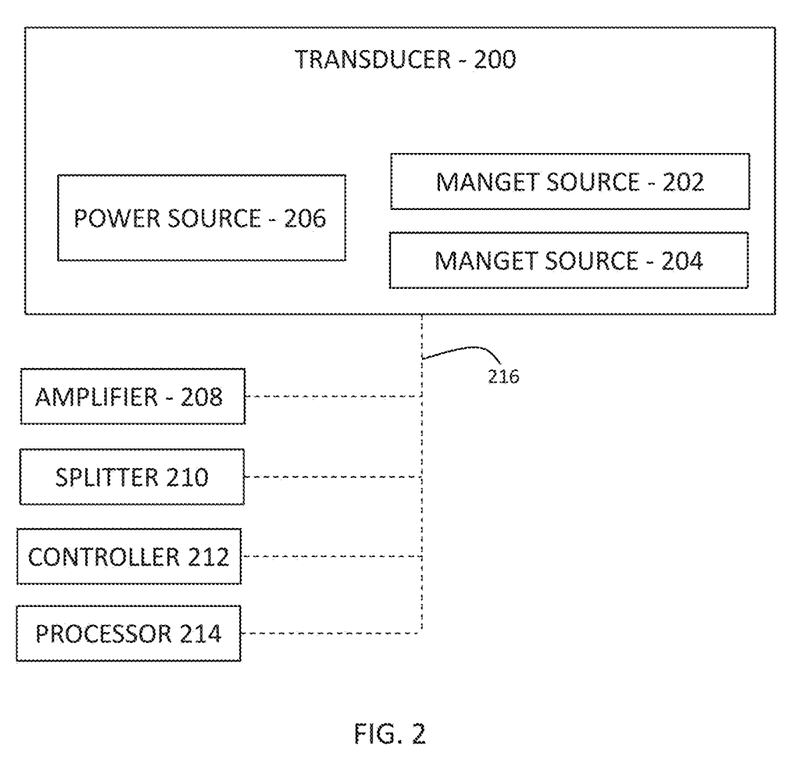
FIG. 2 is a block diagram depicting an exemplary transducer used as part of a system for at least partially implementing the method of FIG. 1.
Figure 3:
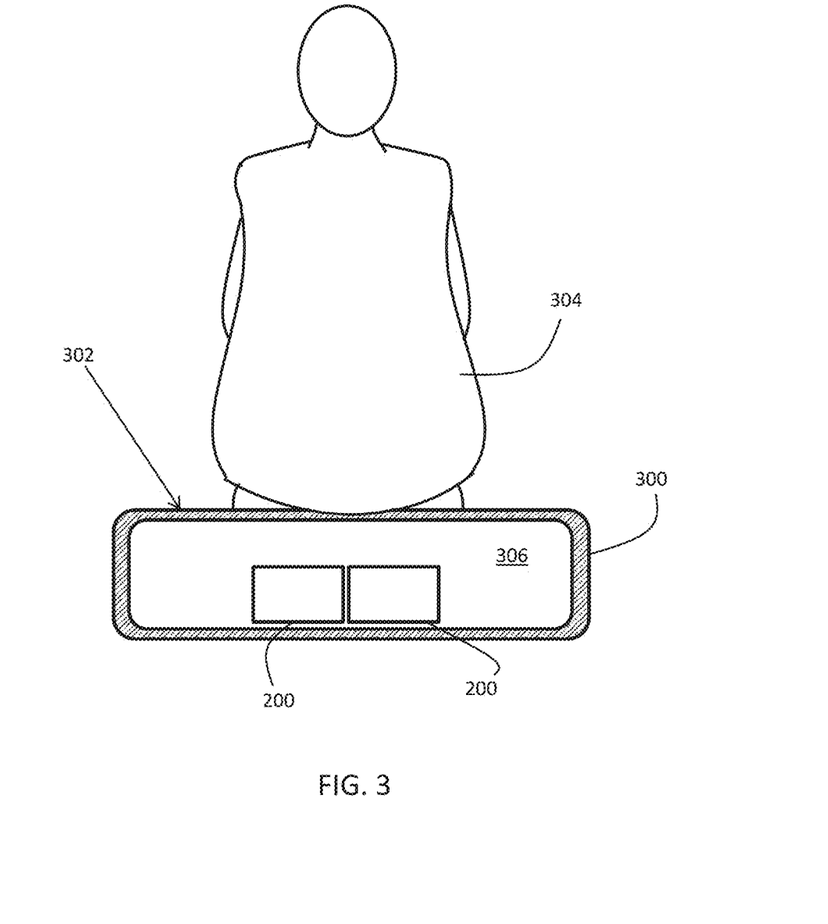
FIG. 3 is an elevational cross-sectional view of a device used for at least partially implementing the method of FIG. 1.

Referring to FIG. 1, a process-flow diagram illustrating one embodiment of the process of interrupting the life cycle of sperm is shown. FIG. 2 shows a block diagram of an exemplary transducer 200 utilized for effectuating the aforementioned process. FIG. 3 depicts an elevational, partially cross-sectional, view of a cushion 300 used in connection with the transducer 200 to advantageously direct energy to the entire male reproductive system including, but not limited to, the testes, epididymal tubules or ejaculation ducts of a user 304 to render a sperm transported therein immotile in accordance with one embodiment of the present invention. FIGS. 1-3 show several advantageous features of the present invention, but, as will be described below, the invention, specifically the process and assembly effectuating said process, can be provided in several shapes, sizes, combinations of features and components, and varying numbers and functions of the components. The first example of the process of interrupting the life cycle of sperm, as shown in FIG. 1, begins at step 100 and immediately proceeds to the next step 102 of subjecting a user to a first treatment session in a male birth-control cycle to render a plurality of sperm transported within the user to be immotile or otherwise nonviable. The first treatment session includes one or more sub-steps that includes a mature-sperm inhibition step embodied, at least in part, in step 114 of FIG. 1. The process continues to the next step 104 of subjecting the user to a second treatment session within the male birth-control cycle before a sperm-maturation time in which sperm carried by the user are in a mature state. The "mature state" is herein defined as seventy-four days from a sperm's initial generation in the Sertoli cells of the seminiferous tubules in a user. The second treatment session also includes the mature-sperm inhibition step. The process may continue to the next step 106 of subjecting the user to an "$N^{th}$" treatment session, wherein $N^{th}$ represents any positive integer number greater than two in order to beneficially effectuate a continuing male birth-control cycle desirable for many users. The process may then terminate at step 118.

In one embodiment, the sperm-maturation time is within thirty days after subjecting the user to the first treatment session embodied in step 102 in the male birth-control cycle to prevent any sperm resident within the user from maturing. Thirty days also provides a period that is memorable to the user in order to effectuate the male birth-control process. In other embodiments, the sperm-maturation time may be sixty days, seventy-four days, or any other time before the maturation of the sperm.

As shown in FIG. 1, a sub-step of the first treatment session—or any other treatment session the user is subjected to—includes a mature-sperm inhibition step 108 of providing at least one transducer 200—depicted in the block diagram of FIG. 2. Following step 108, the next step 110 may include providing a cushion 300, or other weight-support device, that may encapsulate or otherwise cover the transducer 200. Next, the process continues to step 112 where the buttocks of the user 304 are positioned on a top surface 302 of the cushion 300.

Next, the process includes the step 114 of emitting—producing or otherwise discharging—an amount of energy for a predetermined period of time through at least one transducer 200. Advantageously, this emitted amount of energy, as further described below, is transferred to the male-reproductive system, which includes either the epididymal tubules or ejaculation ducts of the user, to provide a non-invasive method stimulating the sperm in a manner such that they die, are otherwise rendered immotile, and are reabsorbed into the user's body. The result is a cost-effective, efficient, and non-invasive method and system of preventing or inhibiting the reproductive viability of sperm that many users find desirable.

A block schematic diagram, shown in FIG. 2, depicts the exemplary transducer 200 that converts a signal in one form of energy to another form of energy. These energy types may include electrical, electromagnetic, mechanical, chemical, acoustic, and thermal energy, among others. Transducers are well-known in the art. In one embodiment, the transducer 200, as shown in FIG. 2, may consist of two magnetic sources 202, 204 each operable to generate a magnetic field. One of the magnetic sources 202, 204 is what may be referred to as a "permanent magnet," such as a naturally metallic material, e.g., iron, cobalt, etc., that generates a magnetic field ranging from approximately 5 mT (milliTeslas) to 3 T (Teslas). Another of the magnetic sources 202, 204 is what may be referred to as a "conditional magnet" or "electromagnet," and includes a metallic coil that is operable to receive an electric current from a power source 206 and effectively induces a magnetic field. Similar to the permanent magnet, the magnetic field of the conditional magnet may range from approximately 5 mT (milliTeslas) to 3 T (Teslas). In other embodiments, the magnetic sources 202, 204 may both be conditional magnets.

The magnetic sources 202, 204 are coupled to one another through a suspension member operable to allow one of the magnetic sources 202, 204 to oscillate with respect to one another via attractive and repelling magnetic forces. The resultant oscillation of the magnetic sources 202, 204 produces energy, e.g., vibrations, with a particular frequency and that energy is amplified when subject to a medium, e.g., air, clothing, or a user's skin. The energy is emitted for a predetermined period of time depending on the users and environmental conditions, e.g., material through which the energy propagates through. In one embodiment of the present invention, a frequency in a range between approximately 20 to 20,000 Hz is generated. Advantageously, the present invention is operable within the acoustic range of frequencies, as opposed to ultrasound frequencies, which reduces the likelihood of damage to human tissue(s) and organ(s) due to overexposure to such frequency ranges. Additionally, acoustic range of frequencies also reduces the likelihood of damage to human tissue(s) and organ(s) that may occur from resultant heat production from molecular frictional forces.

In other embodiments, the amount of energy may be generated and emitted via the use of a vibrating and electrically conductive medium flanked by variably charged plates induced with an electrical current, or with a structural apparatus movable with a mechanical actuator or motor. In additional embodiments, the modulated amount of energy may be produced via focused electrical stimulation.

With reference to FIGS. 1 and 3, the cushion 300 can be seen encapsulating or otherwise in a covering relationship with one or more transducers 200 operable to emit an amount of energy. The cushion 300 has a top surface 302 sized to receive the buttocks of the user 304. In one embodiment, the top surface 302 is approximately 3×3 feet and is of a fabric or polymeric material of general thickness of approximately 1/16 of an inch. In other embodiments, the material of the cushion may vary, but the below-described operational conditions of the transducer may vary. The emitted energy from the transducers 200 propagates through a medium 306, e.g., air or cushion material, within the cushion 300 to its directed location, i.e., the epididymal tubules and ejaculation ducts of the user 304. Propagate is hereinafter defined as transmitting through a medium, e.g., air.

With reference back to FIG. 1, the process continues to step 116, where the emitted amount of energy is directed at least at a predetermined minimum intensity sufficient to propagate the emitted amount of energy to either the epididymal tubules and ejaculation ducts of the user. The emitted energy is "directed" to the user, placing the user in a constant coupling configuration with the transducer and directing the emitted energy such that it may reach the skin of the user, and ultimately propagate to the target zones. This "constant coupling configuration" is placing the user 304 in a position such that the emitted energy from the transducer 200 is relayed consistently to the user 304 while exposed to the below-specified conditions, for the predetermined period of time. Further, constant coupling configuration is not, necessarily, the direct coupling of the user 304 to the transducer 200, but rather may also be indirect coupling. In one embodiment, the constant coupling configuration may occur through having the user 304 place his or her buttocks on the upper surface 302 of the cushion 300 for the predetermined period of time. In other embodiments, a portable, hand-held, device encapsulating or otherwise incorporating a transducer will be in direct contact with the user's skin and/or clothing for the predetermined period of time.

In one embodiment, the amount of energy emitted from the transducer 200 "directed" to the user 304 in that a back-and-forth motion of the transducer 200 is substantially aligned with, i.e., deviating within 4" from, the center of mass of the user's 304 testicles. In other embodiments, when a plurality of transducers 200 are used to effectuate the process, it is the median of the length of transducers 200 are substantially aligned with the center of mass of the user's 304 testicles.

One testing environmental condition, in which the inventive process was found to have rendered targeted sperm immotile or otherwise nonviable, includes the ambient air with a relative humidity from approximately 30-40%. In one embodiment, the at least one transducer 200 emits an amount of energy that is in the form of an oscillating, i.e., moving back and forth between at least two points, sound pressure wave in an acoustic frequency range, i.e., 10-20,000 Hz. This transducer 200 may consist of a modified speaker assembly devoid of a "cone," metal frame for the cone, or other suspension medium for the cone, and includes the at least two magnets, 202, 204, one which may consist of "voice coil" with a diameter of approximately 1 inch. The voice coil may be operable to receive power up to approximately 20 watts and has a 25 mm nominal impedance with approximately 4 ohms resistance. The user 304 is placed in a constant coupling configuration with the transducer 200 through the cushion medium 300 (which facilitates generating the sound waves from the operating transducer 200). In the current preferred embodiment, the sound pressure wave is emitted from the transducer 200 for approximately 36 minutes (i.e., a predetermined period of time) while the user is in the constant coupling configuration with the cushion 300. The sound pressure wave is emitted at a frequency of approximately 10 Hz and has an intensity (i.e., a predetermined minimum intensity) of approximately 10 watts (or 50% of the maximum output), which testing has shown is sufficient to propagate the emitted amount of energy to at least one of the epididymal tubules and ejaculation ducts of the user 304 to render a sperm transported therein immotile or otherwise nonviable.

Figure 4:
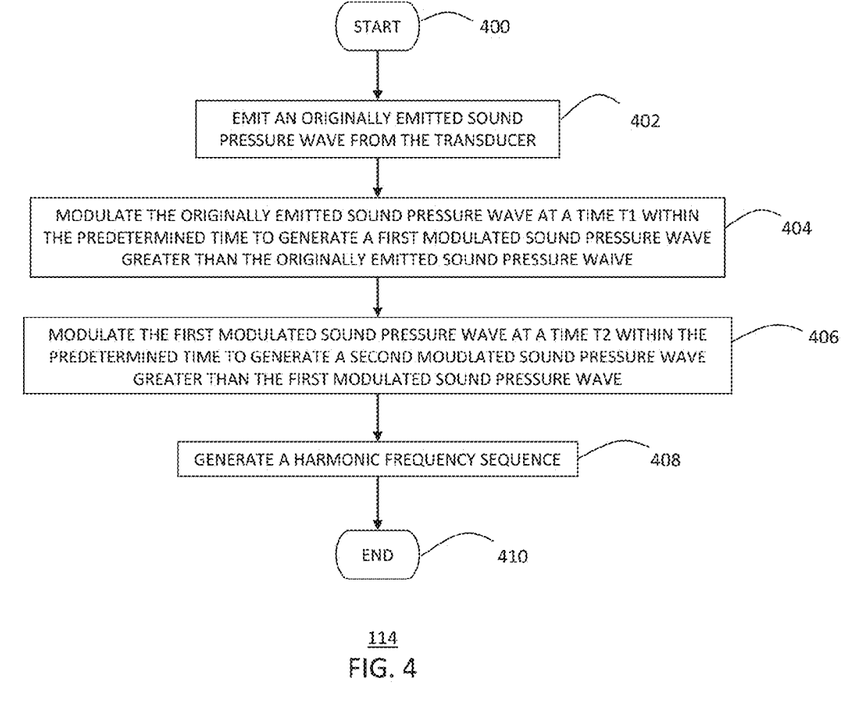
FIG. 4 is a process-flow diagram depicting sub-steps involved in the emission of energy step 114 of FIG. 1 in accordance with an embodiment of the present invention.

With reference now to FIGS. 3 and 4, step 114 may include the sub-step 402 of initially emitting a sound pressure wave from the transducer(s) 200. Next, the process continues to the advantageous sub-step 404 of modulating, i.e., increasing or decreasing the frequency of, the oscillating sound pressure wave, i.e., emitted energy, from the transducer 200 at a point in time $T_1$ that falls within the predetermined period of time to generate a first modulated sound pressure wave. Testing has shown, however, that more effective results, i.e., increased probability of immotile or non-viable sperm, are effectuated by modulating the emitted sound pressure wave (i.e., the initially emitted amount of energy) to a greater frequency, i.e., to create a first-modulated sound pressure wave. Further experimentation has revealed that superior results are effectuated by carrying out the sub-step 406 of modulating the frequency of the first modulated sound pressure wave at a point in time $T_2$ within the predetermined period of time to generate a second modulated sound pressure wave having a frequency greater than the frequency of the first modulated sound pressure wave.

For example, if the transducer(s) 200 emits an initial sound pressure wave of approximately 10 Hz during an allotted predetermined time interval of approximately 30 minutes, then, at some after period of time during the 30 minutes, e.g., 15 minutes, the same or another transducer(s) 200 may then emit another sound pressure wave, i.e., a "first modulated sound pressure wave," at a frequency of approximately 12 Hz in lieu of or supplemental to the originally emitted frequency. Then, after the 12 Hz frequency, e.g., at approximately 25 minutes after the originally emitted sound pressure wave, the same or another transducer(s) 200 may then emit another sound pressure wave, i.e., a "second modulated sound pressure waive," at a frequency of approximately 14 Hz in lieu of or supplemental to the originally emitted frequency and/or the first modulated sound pressure wave. This process may vary in time, e.g., may span in time for approximately 72 minutes, and in frequency based on environmental and material propagation conditions.

As shown below in Table 1, however, it is preferred that the amount of energy emitted from the transducer 200 is of a plurality of oscillating energy pressure waves in a predetermined harmonic frequency sequence, as embodied in sub-step 408 of FIG. 4.

TABLE 1

| Time | Time Interval (min) | Frequency (Hz) |
| --- | --- | --- |
| $T_1$ | 0 | 10 |
| $T_2$ | 6 | 11 |
| $T_3$ | 12 | 12 |
| $T_4$ | 18 | 13 |
| $T_5$ | 24 | 14 |
| $T_6$ | 30 | 15 |
| $T_7$ | 36 | 14 |
| $T_8$ | 42 | 13 |
| $T_9$ | 48 | 12 |
| $T_{10}$ | 54 | 11 |
| $T_{11}$ | 60 | 10 |

Therefore, at $T_1$, i.e., at time "0," the at least one transducer 200 emits a frequency of 10 Hz, for example. Then, at the above listed time intervals, i.e., $T_2$, $T_3$, etc., one or more transducers 200 vary the emitted frequency ranges, in whole or in part, to effectuate propagation of the sound waves through the cushion, through the user's skin, and ultimately to either the epididymal tubules or ejaculation ducts of the user 304. The emitted frequencies are "harmonic" when the transducer(s) 200 emit a plurality of frequencies simultaneously, and one of the plurality of frequencies is a component frequency of the base, also referred to as the "fundamental," frequency. Using Table 1, for example, the exemplary series of frequencies is a harmonic series when a fundamental frequency "f" of 10 Hz is emitted at $T_1$, and subsequently, i.e., at $T_2$ and $T_3$, emitted frequencies, hereinafter referred to as "harmonic frequencies," are emitted based on a function of the fundamental frequency, e.g., (1+f). Therefore, in addition to harmonics being generated through multiplying an integer with the fundamental frequency such that the generated frequencies are all periodic at the fundamental frequency, a series may be "harmonic" for the purposes of this disclosure when at least two frequencies, in addition to the fundamental frequency, are emitted and dictated by a function dependent on the fundamental frequency. In other variations of the present invention, the frequency levels may vary outside of those described in Table 1, may be emitted by transducer(s) 200 at varying time intervals, and may be escalading or increasing in frequency.

Furthermore, the above frequencies described in Table 1 may be emitted at a predetermined minimum intensity of the equivalent of approximately five watts, e.g., approximately 37 dBm (decibels), 5 Joules/sec, 17 BTU/hr. The above values are said to be "predetermined" in that the value(s) are initially set before the initiation of a process. In other embodiments of the present invention, the values will be dictated based on certain feedback protocols utilizing sensors and other devices for detecting qualitative and/or quantities properties associated the emitted energy as it propagates through the cushion 300 and/or the user 304. In other embodiments of the present invention, however, the actual intensity of the energy emitted from the transducer(s) 200 may vary and/or the minimum intensity of the waves may be less than the equivalent of approximately 9 watts.

Advantageously, further testing has shown that a higher percentage of immotile and nonviable sperm are effectuated when the amount of energy is of a sound pressure wave having a sinusoidal waveform. This is at least in part because, when used with additional sine waves of varying magnitude and/or phase, the waveform substantially retains its shape.

Referring briefly back to FIG. 3, in addition to the use of a transducer(s) 200, the present invention may utilize amplifier(s) 208, a splitter 210, a controller 212, and/or a processor 214, in addition to other components, to effectuate the delivery of the emitted energy. One or more of the above components 200, 208, 210, 212, 214, may be, directly or indirectly, communicatively coupled, via wiring 216 or over a network, to one other to effectuate the above-described processes automatically, via a program executable by the processor 214, or a manually by a user. One or more of the above components 200, 208, 210, 212, 214, may be housed together or housed separate from one another.

Figure 5:
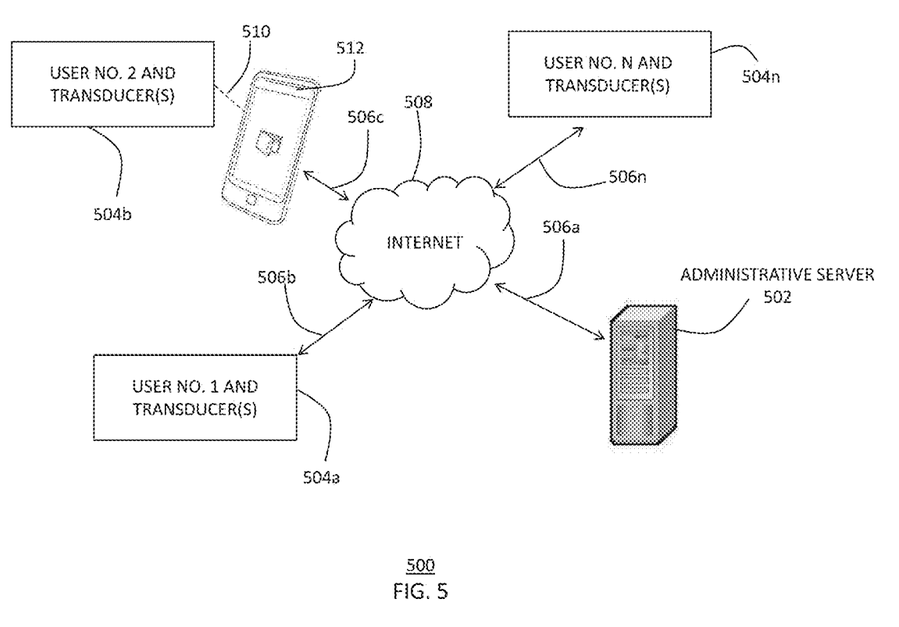
FIG. 5 is a schematic block diagram of an exemplary data processing network having a computing device, at least one transducer, and an administrative server communicatively coupled to each other at least partially over the network in accordance with an embodiment of the present invention.

Specifically, with reference now to FIGS. 2 and 5, in one embodiment of the present invention, the process includes providing a controller 212 electrically coupled, e.g., through wiring 216, to the at least one transducer 200. The controller 212 is operably configured to provide timing and duration optimization to the one or more transducer(s) 200 so as effectuate delivery of the emitted energy to the user 314.

In one embodiment, the processor 214 executes a program that includes the steps of initiating (1) a first phase, (2) a modulation phase, and (3) a second phase. The first phase includes the emission of the amount of energy through the at least one transducer 200 and the second phase includes a cessation of the emission of the amount of energy through the at least one transducer 200 at a conclusion of the predetermined period of time. The modulation phase includes emitting a series of modulated amounts of energy with a plurality of oscillating energy pressure waves, of varying frequencies, in the acoustic frequency range as discussed above. The above-described phases may be initiated manually by a user, or may be carried out automatically based on the happening of one or more events, e.g., sensing the user 304 placing his or her buttocks on the cushion 300.

Figure 6:
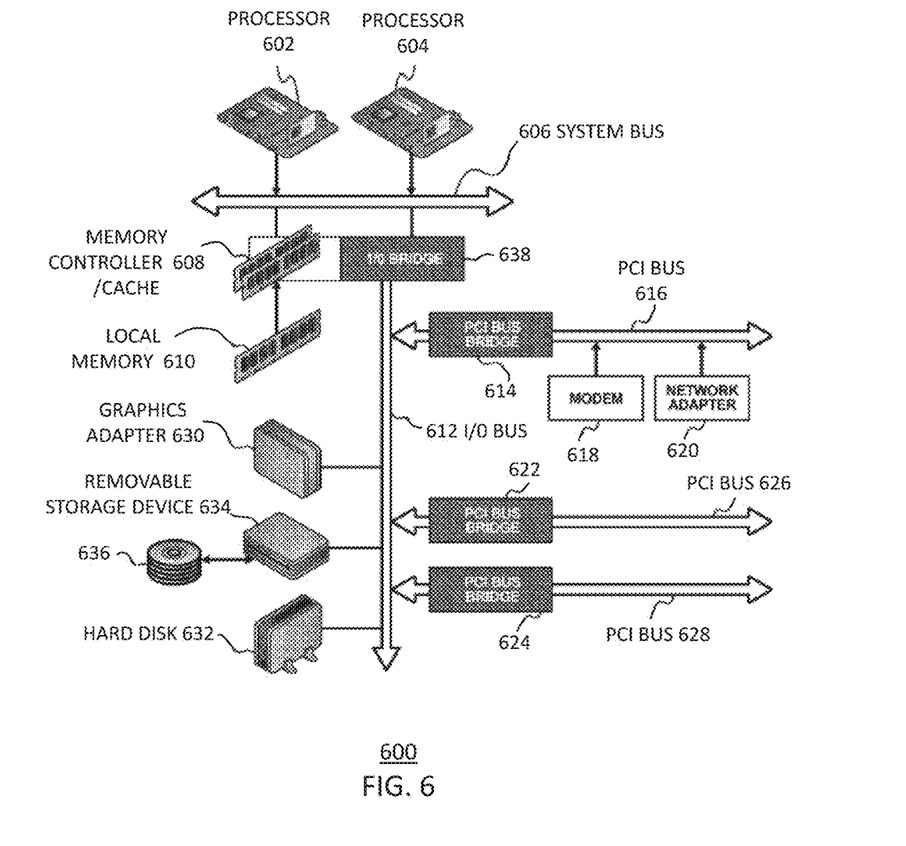
FIG. 6 is a block diagram of a data processing system that may be implemented as a network device, such as the administrative server shown in FIG. 5, in accordance with an embodiment of the present invention.

With reference now to FIGS. 5 and 6, in further embodiments the program is only executed by the processor upon receiving an initiation signal that directs the processor to initiate the first phase of the program. As shown in FIG. 5, the initiation signal may be received and/or communicated to a computing device 512 of a user 304 by an administrative server 502 that may be operated and managed by a party other than the user 304. In this manner, the generation or communication of the initiation signal by the server 502 may be conditioned upon the payment of a periodic or one-time fee. Moreover, one or more user profiles may be established and resident on the computing device 512, e.g., mobile phone, of the user 304 or on the server 502 so that a payment medium may be associated therewith and utilized for payment of the aforementioned fee.

The initiation signal, or any other signal generated by the server 502 to direct the processor to carry out one or more phases of the program, may be communicated over a network 500. In the depicted example of FIG. 5, network 500 can include the Internet 508, which represents a worldwide collection of networks and gateways that use the TCP/IP suite of protocols to communicate with one another. At the heart of the Internet 508 is a backbone of high-speed data communication lines between major nodes or host computers, consisting of thousands of commercial, government, educational and other computer systems that route data and messages. Of course, network 500 also may be implemented as a number of different types of networks, such as for example, an Intranet, a local area network (LAN), or a wide area network (WAN). FIG. 5 is intended as an example, and not as an architectural limitation for the present invention. The network 500 includes connections 508a-n, which are the medium used to provide communication links between various devices and computers, or computing devices, connected together within the network 500. The connections 508a-n may be wired or wireless connections. A few exemplary wired connections are cable, phone line, and fiber optic. Exemplary wireless connections include radio frequency (RF) and infrared radiation (IR) transmission. Many other wired and wireless connections are known in the art and can be used with the present invention. As shown in FIG. 5, the computing device 512 may be communicatively coupled, through a link 510, to one or more transducer(s) 504a-n to effectuate the above-described process embodied in FIG. 1.

The network 500 may include additional servers and other devices and entities not shown. In the depicted example, the computing device 512, that is represented as a mobile computing device, and/or the processor 214—which may be resident on the computing device 512—communicates with the administrative server 502 over the network 500. Furthermore, the administrative server 502 may also be communicatively coupled, through one or more links 506a-n, to one or more transducer(s) 504a-n of various users to effectuate the above-described process embodied in FIG. 1 individual for a plurality of users. This type of data exchange may occur through the Internet 508, or another wireless or wired data exchange method, e.g., Bluetooth, radio frequency identification (RFID), or near field communications (NFC). Moreover, any of the depicted network entities, in addition to communicating with each other over the network 500, are, in some embodiments, also able to communicate in a peer-to-peer relationship using wired or wireless links. In embodiments of the present invention, various computing entities located on the network 500 may perform all, or some, of the above-described steps of the present invention represented in FIG. 1 or otherwise disclosed herein.

Referring to FIG. 6, a block diagram of a data processing system 600 that may be implemented as a server or other computing device such as the electronic computing device 512 or server 502. Further, the system 600 may be implemented, whether in whole or in part, through a personal computer or terminal/computer/display associated with such computing device 512 or server 502, as shown in FIG. 5, in accordance with embodiments of the present invention. The data processing system 600 may be a symmetric multiprocessor (SMP) system including a plurality of processors 602 and 604 connected to system bus 606. Alternatively, a single processor system may be employed. Also, connected to system bus 606 is memory controller/cache 608, which provides an interface to local memory 610. An I/O bus bridge 638 is connected to system bus 606 and provides an interface to I/O bus 612. The memory controller/cache 608 and I/O bus bridge 638 may be integrated as depicted. The processors 602, 604 in conjunction with memory controller 608 control what data is stored in memory 610. The processor 602 and/or 604 and memory controller 608 can serve as a data counter for counting the rate of data flow to the memory 610 or from the memory 610 and can also count the total volume of data accessed to or from the memory 610. The processor 602 or 604 can also work in conjunction with any other memory device or storage location.

Peripheral component interconnect (PCI) bus bridge 614 connected to I/O bus 612 provides an interface to PCI local bus 616 that may be employed for one or more of the displays utilized with the computing device 512. In addition, a number of modems 618, or wireless cards, may be connected to PCI bus 616. Typical PCI bus implementations will support four PCI expansion slots or add-in connectors. PCI includes, but is not necessarily limited to, PCI-X and PCI Express components. Communication links to the network 500 of computers or computing devices in FIG. 5 may be provided through the modem 618 and network adapter 620 connected to PCI local bus 616 through add-in boards.

Additional PCI bus bridges 622 and 624 provide interfaces for additional PCI buses 626 and 628, from which additional modems or network adapters may be supported. In this manner, the data processing system 600 allows connections to a multiple network of computers and/or computing devices. A graphics adapter 630 and hard disk 632 may also be connected to I/O bus 612 as depicted, either directly or indirectly.

Those of ordinary skill in the art will appreciate that the hardware depicted in FIG. 6 may vary. For example, other peripheral devices, such as optical disk drives and the like, also may be used in addition to or in place of the hardware depicted. The depicted example is not meant to imply architectural limitations with respect to the present invention.

The steps of the present invention, which are explained in more detail above, can be embodied in a computer program that is executable by one of the above-described processors 602, 604. Computer programs (also called computer control logic) are stored in memory such as main memory 610, removable storage drive 634, removable media 636, hard disk 632, and signals. Such computer programs, when executed, enable the computer system to perform the features of the present invention as discussed herein. In particular, the computer programs, when executed, enable the processor 602 and/or 604, which may also be the processor 214, to perform the steps of the present invention.

In this document, the terms "computer program medium," "computer usable medium," and "computer readable medium" are used to generally refer to media such as main memory 610, removable storage drive 634, removable media 636, hard disk 632, and signals. These computer program products are means for providing software to the computer system. The computer readable medium allows the computer system to read data, instructions, messages or message packets, and other computer readable information from the computer readable medium. The computer readable medium, for example, may include non-volatile memory, such as Floppy, ROM, Flash memory, Disk drive memory, CD-ROM, and other permanent storage. It is useful, for example, for transporting information, such as data and computer instructions, between computer systems. Furthermore, the computer readable medium may include computer readable information in a transitory state medium such as a network link and/or a network interface, including a wired or wireless network, which allows a computer to read such computer readable information.

As such, the electronic computing device 512 may also include a computing means, e.g., a processor 214, and a storing means, e.g., a memory. The processor is operable to run one or more programs/applications and interfaces associated with the electronic computing device 512 or stored on the memory in order to effectuate the data transfer and communications required by the present invention.

What is claimed is:

1. A method of interrupting a life cycle of sperm, the method comprising:
    subjecting a user to a first treatment session in a male birth-control cycle, the first treatment session including a mature-sperm inhibition step of emitting, through at least one transducer having energy supplied thereto from an energy source, an amount of energy in the form of an oscillating sound pressure wave in an acoustic frequency range, for a predetermined period of time that is directed to at least one of an epididymal tubules and an ejaculation ducts of the user, via a constant coupling configuration of the transducer in substantial alignment with and within four inches of the center of mass of the testes of the user, rendering a plurality of sperm transported therein to be immotile; and
    subjecting the user to a second treatment session within the male birth-control cycle before a sperm-maturation time whereby sperm carried by the user are in a mature state, the second treatment session including the mature-sperm inhibition step.

2. The method according to claim 1, further comprising:
    providing a controller electrically coupled to the at least one transducer, the controller operably configured to provide timing and duration optimization to the at least one transducer.

3. The method according to claim 2, further comprising:
    executing a program stored on a non-transitory computer-readable medium, by a processor communicatively coupled to the controller, the program having steps that include initiating a first phase that includes the emission of the amount of energy through the at least one transducer, a modulation phase that includes emitting a series of modulated amounts of energy with a plurality of oscillating sound pressure waves, of varying frequencies, and a second phase that includes a cessation of the emission of the amount of energy through the at least one transducer at a conclusion of the predetermined period of time.

4. The method according to claim 3, further comprising:
    receiving, at a processor resident on a computing device of a user, an initiation signal directing the processor communicatively coupled to the controller to initiate the first phase of the program.

5. The method according to claim 2, further comprising:
    executing a program stored on a non-transitory computer-readable medium, by a processor communicatively coupled to the controller, the program having steps that include initiating a first phase that includes the emission of the amount of energy through the at least one transducer and a second phase that includes a cessation of the emission of the amount of energy through the at least one transducer at a conclusion of the predetermined period of time.

6. The method according to claim 1, wherein the mature-sperm inhibition step further comprises:
    providing a cushion having a top surface sized to receive buttocks of the user, wherein the cushion is in a covering relationship with the transducer.

7. The method according to claim 6, wherein the mature-sperm inhibition step further comprises:
    positioning the buttocks of the user on the top surface of the cushion.

8. The method according to claim 6, wherein the mature-sperm inhibition step further comprises:
    the cushion encapsulates the transducer.

9. The method according to claim 1, wherein the mature-sperm inhibition step further comprises:

modulating a frequency of the oscillating sound pressure wave at a point in time $T_1$ within the predetermined period of time to generate a first-modulated sound pressure wave having a frequency greater than the frequency of the oscillating sound pressure wave.

10. The method according to claim 9, wherein the mature-sperm inhibition step further comprises:

modulating the frequency of the first-modulated sound pressure wave at a point in time $T_2$ within the predetermined period of time to generate a second-modulated sound pressure wave having a frequency greater than the frequency of the first-modulated sound pressure wave.

11. The method according to claim 10, wherein:

the point in time $T_2$ is later than the point in time $T_1$.

12. The method according to claim 1, wherein the mature-sperm inhibition step further comprises:

directing the amount of energy at a predetermined minimum intensity sufficient to propagate the amount of energy to the at least one of an epididymal tubules and an ejaculation ducts of the user to render the plurality of sperm transported therein to be immotile.

13. The method according to claim 12, wherein:

the predetermined minimum intensity of the amount of energy is an equivalent of approximately five watts.

14. The method according to claim 1, wherein the oscillating sound pressure wave further comprises:

a series of modulated amounts of energy for the predetermined period of time.

15. The method according to claim 14, wherein:

the plurality of oscillating sound pressure waves are of varying frequencies.

16. The method according to claim 1, wherein:

the sperm-maturation time is within seventy-four days after subjecting the user to the first treatment session in the male birth-control cycle.

17. The method according to claim 1, wherein:

the sperm-maturation time is within sixty days after subjecting the user to the first treatment session in the male birth-control cycle.

18. The method according to claim 1, wherein:

the sperm-maturation time is within thirty days after subjecting the user to the first treatment session in the male birth-control cycle.

19. The method according to claim 1, wherein:

the amount of energy is of at least three oscillating sound pressure waves in a predetermined harmonic frequency sequence.

* * * * *